United States Patent [19]
Hamouda et al.

[11] Patent Number: 5,749,259
[45] Date of Patent: May 12, 1998

[54] APPARATUS FOR SIMULATING THE THERMOREGULATORY RESPONSES OF HUMAN SKIN AND RELATED METHOD FOR PREDICTING FABRIC COMFORT LEVEL

[75] Inventors: Hechmi Hamouda; Roger L. Barker, both of Raleigh, N.C.; Darrin S. Millsaps, Lawrenceville, Ga.

[73] Assignee: North Carolina State University, Raleigh, N.C.

[21] Appl. No.: 439,662

[22] Filed: May 12, 1995

[51] Int. Cl.$^6$ ............................ G01N 25/00; G01N 33/36
[52] U.S. Cl. ............................................. 73/159; 374/109
[58] Field of Search .......................... 374/45, 109; 73/159

[56] References Cited

U.S. PATENT DOCUMENTS

| | | | |
|---|---|---|---|
| 3,075,377 | 1/1963 | Lang | 374/43 X |
| 5,021,280 | 6/1991 | Farnsworth et al. | 428/102 |
| 5,043,209 | 8/1991 | Boisse et al. | 428/233 |

FOREIGN PATENT DOCUMENTS

| | | | |
|---|---|---|---|
| 241083 | 12/1969 | U.S.S.R. | 73/159 |
| 549721 | 3/1977 | U.S.S.R. | 374/45 |

OTHER PUBLICATIONS

Goldman, "Evaluating the Effects of Clothing on the Wearer" *Bioengineering, Thermal Physiology, and Comfort*, (1981) pp. 41–55.

Olesen et al., "Physiological Comfort Conditions at Sixteen Combinations of Activity, Clothing, Air Velocity and Ambient Temperature" *Ashrae Transactions*, reprint No. 2254, vol. 78, Part II, (1972).

Chen, "Heat and Moisture Transfer Properties of Multi-layer Fabric Assemblies", *Ph.D. Dissertation*, North Carolina State University Library, (1994).

Farnworth, "A Numerical Model of the Combined Diffusion of Heat and Water Vapor Through Clothing", *Textile Research Journal*, Nov. 1986, pp. 653–665.

*Primary Examiner*—William A. Cuchlinski, Jr.
*Assistant Examiner*—Willie Morris Worth
*Attorney, Agent, or Firm*—Richard E. Jenkins, P.A.

[57] ABSTRACT

Sweating hot plate apparatus simulating the thermoregulatory behavior of human skin and related method for predicting fabric comfort level with the apparatus. Fabric is placed on the top surface of the apparatus, and selected constant inputs of power flux and water flow are supplied to the apparatus, whereby the surface temperature of the apparatus changes and closely approximates the skin temperature of human subjects having levels of heat generation and sweat production corresponding at the same levels of power flux input and water flow input, respectively.

20 Claims, 15 Drawing Sheets

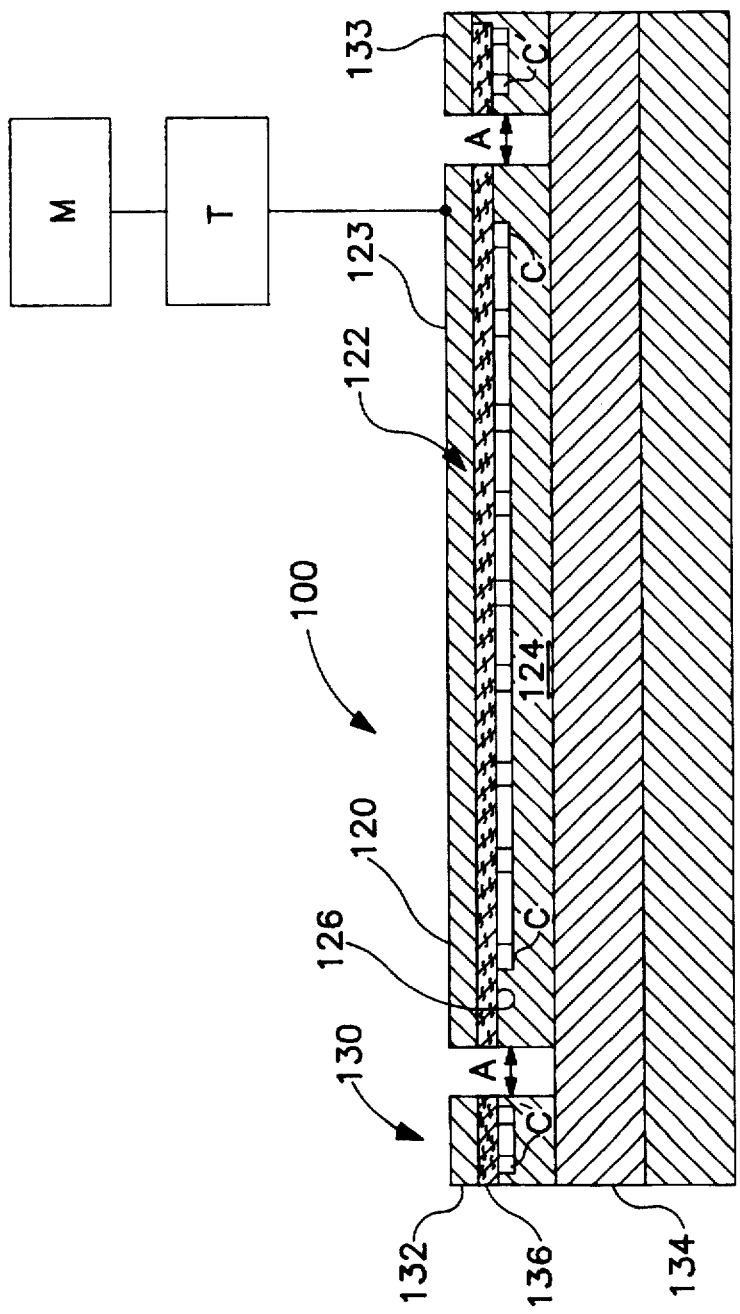
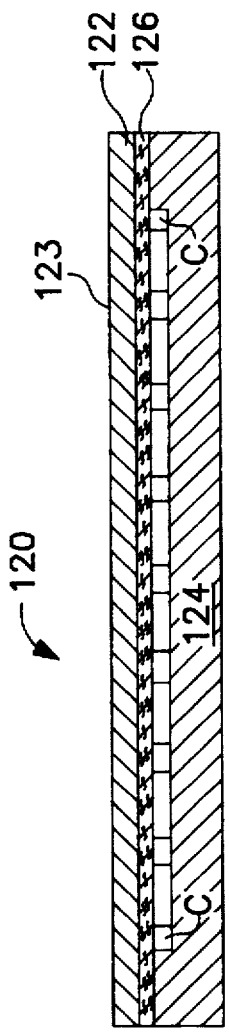
FIG. 1A
FIG. 1B

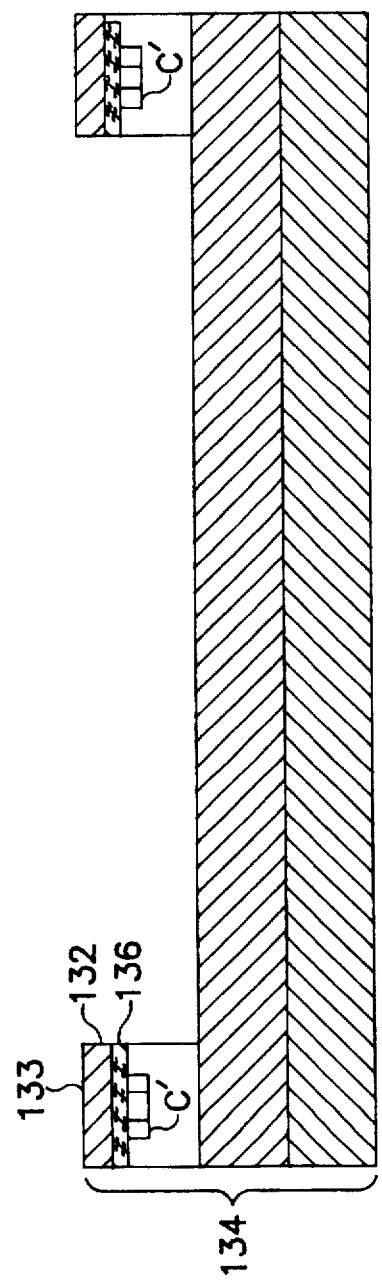

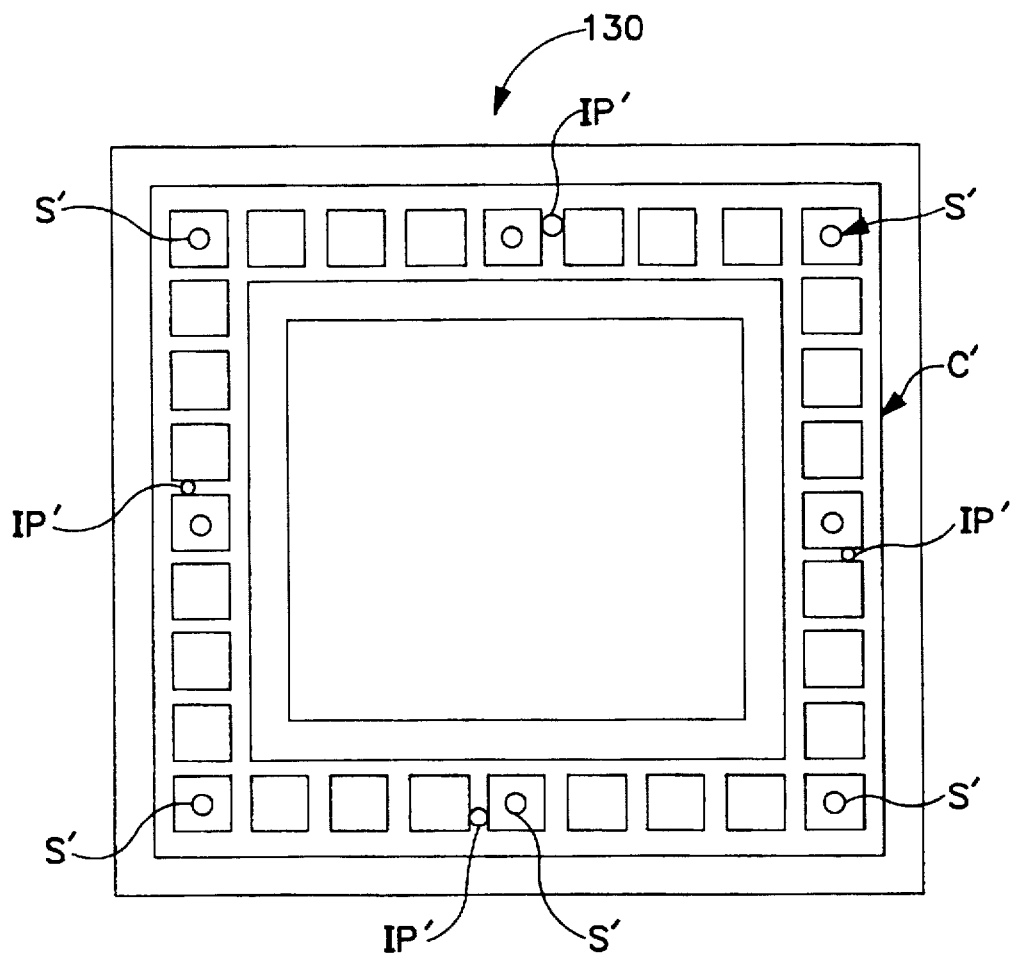
FIG. IE

APPARATUS FOR SIMULATING THE THERMOREGULATORY RESPONSES OF HUMAN SKIN AND RELATED METHOD FOR PREDICTING FABRIC COMFORT LEVEL

DESCRIPTION

1. Technical Field

The present invention relates, in general, to sweating hot plate apparatus used in determining thermal resistance values and moisture vapor resistance values of fabrics, such as those made into clothing for humans. More particularly, the present invention relates to a sweating hot plate apparatus that can be set with a pre-selected thermal input, i.e., electrical flux density, and a pre-selected water input, i.e., flow rate density, so that the top surface of the apparatus changes temperature in order to simulate the skin surface thermoregulatory responses of a human, and as a result of which, when a fabric is placed on the top surface of the apparatus, the thermal comfort of the fabric can be predicted directly.

2. Related Art

Sweating hot plates have been used for years to determine the thermal resistance properties and moisture resistance properties of fabrics. Such traditional sweating hot plates operate by maintaining a constant plate surface temperature, a known water vapor pressure at the surface of the plate, and constant environmental conditions, such as air temperature, humidity, and velocity. With the use of insulation and a surrounding guard, these traditional plates create a 1-dimensional flow of heat through test fabrics. Consequently, the thermal resistance and moisture resistance of fabrics can be calculated employing equations based on the recorded changing power input and changing water input used to maintain the plate surface at a selected temperature and water vapor pressure, respectively.

More particularly, a representative sweating hot plate is described in Farnworth, "A Numerical Model of Combined Diffusion of Heat and Water Vapor Through Clothing", *Textile Res. J.*, Vol. 56, p. 653 (1986). This sweating hot plate is designed to maintain a constant surface temperature of 35° C. and consists of a circular-shaped inner plate, a guard ring plate, and a base plate. The sides of the inner plate are separated from the guard ring plate by a 1 mm air gap and the bottom of the inner plate is separated from the base plate by 50 mm of foam insulation. The guard ring plate and the base plate vent heat flow away from the inner plate in the lateral and the downward directions, respectively. Electrical heaters, connected to DC power supplies, are used to maintain the inner plate at the constant temperature of 35° C., which is determined by a thermistor. All 3 plates are located inside of a heated box to eliminate further heat flow away from the inner plate in any direction other than that upward from the plate surface.

Differential thermocouples, connecting the inner plate to the guard ring plate and to the base plate, indicate when a temperature difference exists among the plates. Additional heaters respond to any such difference in plate temperatures by supplying heat appropriately to maintain the constant surface temperature.

The simulation of sweating is achieved by supplying pure water to the inner plate and the guard ring plate at 4 locations per plate, for a total of 8 water lines. A syringe pump, manually controlled by an operator using potentiometers, feeds each of the 8 water lines, one at a time, using a solenoid valve. Since the inner plate has a surface area of 0.01 m² and only 4 points exist where the water reaches the surface, thin tissue paper is glued to the inner plate. The tissue acts as a wick and helps distribute the water and helps achieve uniform evaporation of the water from the inner plate. The guard ring plate is similarly constructed with 4 points where the water reaches the surface and with tissue paper to help distribute the water.

Further in connection with the water distribution, it should be noted that the sweating hot plate is not maintained completely wet, but rather, is supplied with a limited quantity of water, as set by the operator, to approximate human sweat glands. Therefore, the water vapor pressure at the surface of the sweating hot plate is not saturated at all times. Thus, in order to calculate the moisture vapor resistance of fabrics, Farnworth calculated the vapor pressure as a function of temperature and the total mass per unit area of water vapor.

In contrast to the sweating hot plate described in the above-mentioned article by Farnworth, another sweating hot plate, which is described in Umbach, "Thermophysical Wear Properties of Water-Tight Yet Water Vapor Permeable Non-Woven/Membrane-Laminates", *Bekleidungsphysiologisches Institute*, Index 87 Congress, consists of only 2 plates, not 3 plates. More specifically, the Umbach sweating hot plate apparatus is sold under the trade name SKIN MODEL by Holimetrix of Boston, Mass., and determines the thermal resistance and the moisture vapor resistance of fabric in the following manner.

The central plate is made up of 2 layers, namely a top layer of sintered steel and a bottom layer that is engraved with channels. Since the sintered steel is porous, water supplied to the channels of the apparatus reaches the surface at virtually any point. The channels in the bottom layer allow the water to flow laterally before it passes up through the top plate pores. The central plate is separated from the guard ring plate by a small air gap, and both the central plate and the guard ring plate are maintained at the same constant temperature. Like the sweating hot plate described in the journal article by Farnworth, the sweating hot plate described in the journal article by Umbach employs DC power supplies for the heat source.

Also, of interest are the sweating hot plates described in Goldman, "Evaluating the Effects of Clothing on the Wearer", *Bioengineering, Thermal Physiology, and Comfort*, edited by Cena and Clark, Elsevier Scientific Publishing Company, New York (1981); Kawabata et al., "Application of the New Thermal Tester 'Thermolabo' to the Evaluation of Clothing Comfort", *Proc. 3rd Japan-Australia Joint Symposium*, p. 343 (1985); Olesen et al., "Physiological Comfort Conditions at Sixteen Combinations of Activity, Clothing, Air Velocity, and Ambient Temperature", *ASHRAE Trans.*, reprint no. 2254 (1989); Holmer et al., "Quantification of Heat Balance During Work in Three Types of Asbestos-protective Clothing", *Int. Arch. Occup. Environ. Health*, Vol. 64, p. 243 (1992); Chen, "Heat and Moisture Transfer Properties of Multilayer Fabric Assemblies", *Ph.D. Dissertation*, North Carolina State University Library (1994); and Adams et al., "Effects of Varied Air Velocity on Sweating and Evaporative Rates during Exercise", *J. Appl. Physiol.*, Vol. 73, p. 2668 (1992).

Accordingly, the prior art sweating hot plates do not provide a realistic simulation of human thermoregulatory response, and therefore it would be desirable to provide a sweating hot plate and related method wherein the surface temperature of the plate is not constant but rather varies so that the plate, when used to test fabric placed thereon, will have a changing surface temperature that approximates the changing skin surface temperature of a human whereby the plate may be employed to predict the thermal comfort of the fabric directly.

SUMMARY AND OBJECTS OF THE INVENTION

Thus, the present invention provides a sweating hot plate apparatus, having a top surface adapted to change temperature for simulation of skin surface thermoregulatory responses of a human. The apparatus comprises an inner plate, a guard plate, a fluid input source, a thermal input source, and a temperature sensor. The inner plate includes (a) a fluid permeable top layer having a top surface, (b) a base layer having one or more channels disposed therein, and preferably (c) paper sandwiched between the top layer and the base layer. The guard plate surrounds the circumference and the bottom of the inner plate, and includes (a) a fluid permeable top layer having a top surface, (b) a base layer having one or more channels disposed therein, and preferably (c) paper sandwiched between the top layer and the base layer. The top surface of the sweating hot plate is defined by the top surfaces of the inner and guard plates.

The fluid input source is connected to the base layers of the inner and guard plates to provide a water flow to the channel(s) of the inner and guard plates. The thermal input source is electrically connected to the sweating hot plate to provide a power flux to the inner and guard plates, and the temperature sensor is operatively connected to the surface of the sweating hot plate to determine the temperature thereof.

Additionally, the present invention provides a method for predicting the thermal comfort of a fabric. The method comprises providing a sweating hot plate apparatus, as described in the above two paragraphs. The method further comprises providing a fluid flow through the fluid input source and providing a power flux through the thermal input source at preselected constant levels, respectively, matching a sweating output level and a thermal output level, respectively, obtained from a pretested human. Next, the method comprises placing a fabric on the top surface of the sweating hot plate and observing the changing temperature of the top surface as the temperature approximately matches skin surface temperature changes obtained from the pretested human at the sweating output and the thermal output levels and thereby simulates the skin surface thermoregulatory responses. Lastly, the method comprises comparing the changing temperature of the top surface of the sweating hot plate to the actual changing temperature of the skin surface of the human and determining therefrom the comfort level of the fabric.

Hence, it is an object of the present invention to provide a sweating hot plate and related method wherein the surface temperature of the plate changes.

It is a further object of the present invention to provide a sweating hot plate and related method wherein the inventive plate and related method maintain constant power flux input and water flow input to closely simulate human thermoregulatory response.

Accordingly, it is an advantage of the present invention that when fabric is tested therewith, the comfort of the fabric can be determined directly as if it were being tested with a human being whose skin surface temperature changes.

Some of the objects and advantages of the invention having been stated above, other objects and advantages will become evident as the description proceeds, when taken in connection with the accompanying drawings and laboratory examples as best described below.

BRIEF DESCRIPTION OF THE DRAWINGS

FIG. 1A is a vertical cross-sectional view of the sweating hot plate (not including associated electrical thermal source and water source associated with the sweating hot plate) of the present invention showing the inner plate and the guard plate;

FIG. 1B is a vertical cross-sectional view of the inner plate of FIG. 1A;

FIG. 1C is a vertical cross-sectional view of the guard plate of FIG. 1A;

FIG. 1E is a horizontal cross-sectional view of the guard plate portion of FIG. 1C;

DETAILED DESCRIPTION AND BEST MODE FOR CARRYING OUT THE INVENTION

Referring now to FIG. 1A, illustrated in vertical cross-section is inventive sweating hot plate 100, having inner plate 120 and surrounding guard plate 130. The power source and the water source are not shown, but rather are described below in connection with FIG. 2.

Figure 1D:
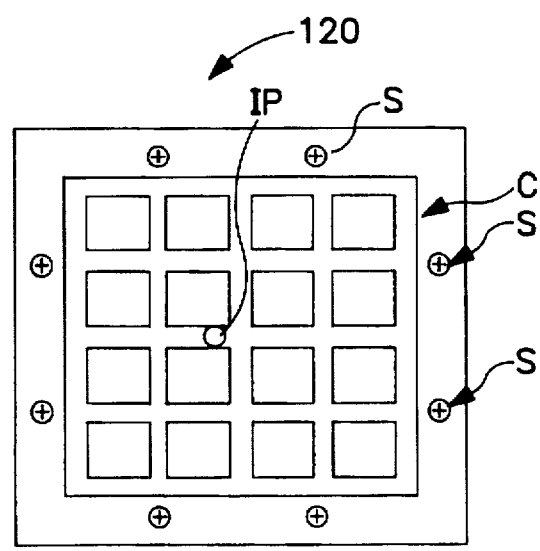
FIG. 1D is a horizontal cross-sectional view of the inner plate portion of FIG. 1B.

To assist in understanding what portion of hot plate 100 comprises inner plate 120 and what portion of hot plate 100 comprises guard plate 130, inner plate 120 is individually illustrated in vertical cross-section in FIG. 1B and guard plate 130 is individually illustrated in vertical cross-section in FIG. 1C. Also, inner plate 120 is individually illustrated in horizontal cross-section in FIG. 1D and guard plate 130 is individually illustrated in horizontal cross-section in FIG. 1E.

As can be seen in FIGS. 1A and 1B, inner plate 120 comprises a top layer or cover 122 of porous, sintered metal, such as stainless steel, with a top surface 123; and a bottom or base 124 of solid metal, such as aluminum, having channels C, preferably with a depth and width ranging from about 1/8 inch (about 0.3175 cm) to about 5/32 inch (about 0.3970 cm), more preferably with a depth and width of about 1/8 inch (about 0.3175 cm), to allow water to flow laterally therethrough. Sintered stainless steel cover 122 is preferably from about 0.75 mm to about 0.85 mm thick, more preferably approximately 0.8 mm thick, whereas aluminum base 124 is preferably from about 0.9 cm to about 1.1 cm thick, more preferably approximately 1 cm thick. Disposed between cover 122 and base 124 is a thin paper layer 126.

As can be seen in FIG. 1D, inner plate 120 has a centrally placed water inlet port IP. Inner plate 120 is suitably square-shaped, having length and width dimensions of 10 cm×10 cm, thereby providing a surface area for top surface 123 of 0.01 m2. Other shapes and sizes are also suitable, and it is not intended to limit the invention to inner plate 120 having a square shape of 10 cm×10 cm.

Similarly, as can be seen in FIGS. 1A and 1C, guard plate 130 includes top layer or cover 132 of porous, sintered metal, such as stainless steel, with a top surface 133; and bottom or base portion 134 of solid metal, such as aluminum, with channels C', preferably with a depth and width ranging from about 1/8 inch (about 0.3175 cm) to about 5/32 inch (about 0.3970 cm), more preferably with a depth and width of 1/8 inch (0.3175 cm), to allow water to flow laterally therethrough. Sintered stainless steel cover 132 is preferably from about 0.75 mm to about 0.85 mm thick, more preferably approximately 0.8 mm thick, and aluminum base 134 is preferably from about 4.0 cm to about 4.5 cm thick, more preferably approximately 1.0 cm thick. A thin paper layer 136 is disposed between cover 132 and base 134.

As can be seen in FIG. 1E, guard plate 130 has 4 water inlet ports IP'. Guard plate 130 is also suitably of a square shape (see FIG. 1E), having outer dimensions of 20 cm×20 cm, thereby providing a surface area for top surface 133 of 0.0292 m$^2$. Other shapes and sizes are also suitable, and it is not intended to limit the invention to guard plate 130 having a square frame shape with outer dimensions of 20 cm×20 cm.

Small air gap A (see FIG. 1A), which may be from about 2 mm to about 2.5 mm and most suitably is approximately 2 mm, is provided between the sides of inner plate 120 and the sides of guard plate 130 to separate inner plate 120 from guard plate 130. Air gap A helps ensure even distribution of heat from sweating hot plate 100 throughout a fabric (illustrated as fabric F in FIG. 2) being tested when the fabric is placed on top of sweating hot plate 100, i.e., on top surfaces 123, 133 of sintered layers 122, 132.

Sintered stainless steel layers or covers 122, 132 have pore sizes typically of 20 microns in nominal diameter, and thus, sintered covers 122, 132 enable water to emerge at nearly any location of top surfaces 123, 133. Preferably, each of paper layers 126, 136 is from about 20 microns to about 50 microns in thickness and made of polyester/woodpulp. To maintain paper layers 126, 136 in place and to keep layers or covers 122, 132 attached to bases 124, 134, respectively, each cover is attached to its respective base with counter-sunk flat head screws S, S' (see FIGS. 1D and 1E) to provide a smooth surface. At the edges of plates 120, 130 where the respective bases and covers meet, there exist small gaps (not illustrated) that separate the respective bases and covers, and to prevent water from escaping through these gaps, a thin layer of tape (not illustrated) is attached to serve as a seal.

Figure 2:
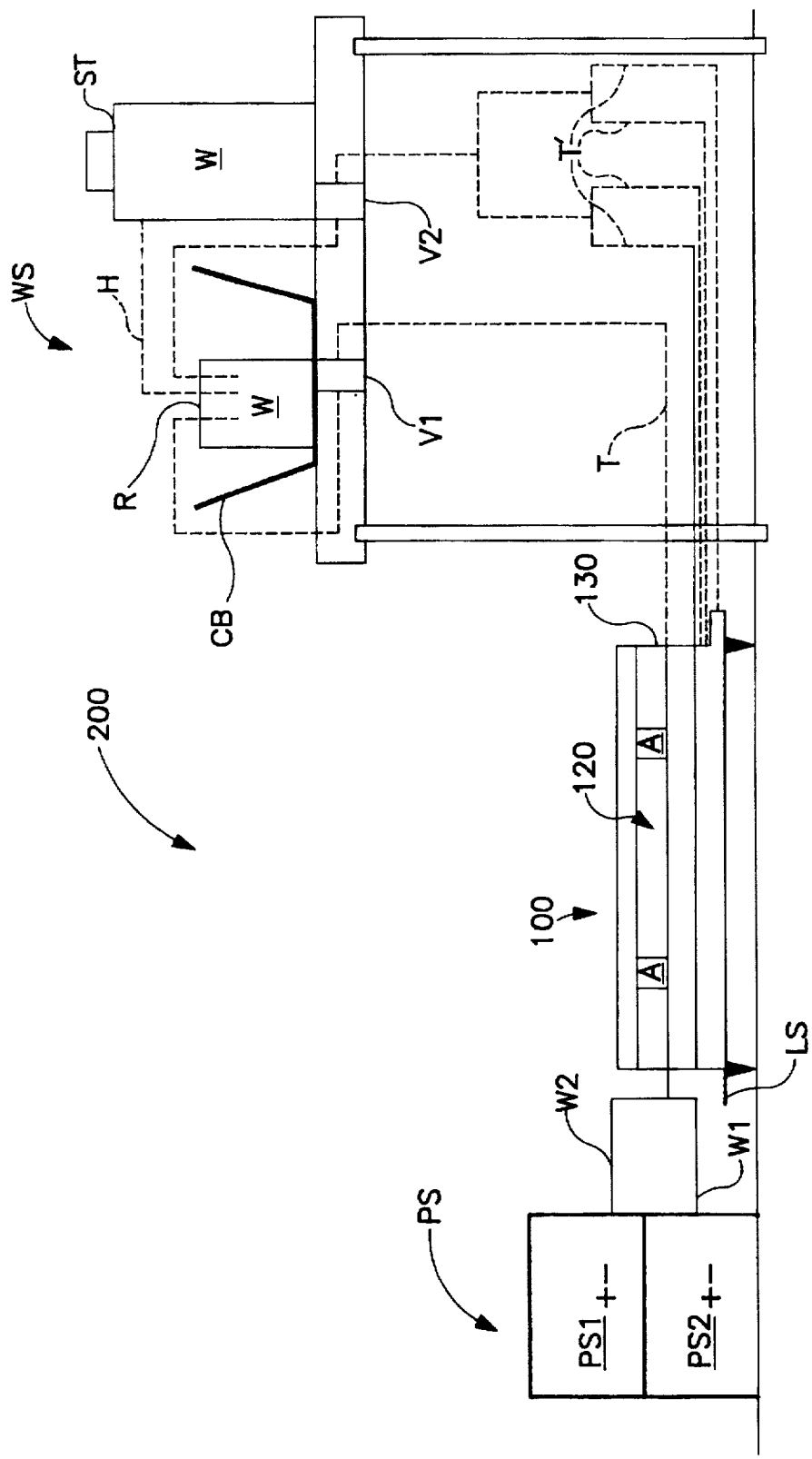
FIG. 2 is a schematic, vertical cross-sectional view of the apparatus of the present invention including the sweating hot plate and associated power source and water source.

With reference now to FIG. 2, illustrated schematically in cross-section is inventive apparatus 200, including sweating hot plate 100 of FIG. 1A, together with associated power source PS and water source WS. Sweating hot plate 100 is shown disposed on leveling stand LS.

Leveling stand LS is suitably a large platform, preferably of 1/4 inch (0.635 cm) thick aluminum and measuring approximately 47 cm×47 cm in length and width so that leveling stand LS is square-shaped. At each of the 4 corners of the square, a bolt (not illustrated) with tapered end is inserted into a tapered hole (not illustrated), to allow for exacting vertical adjustments, and, in turn, for leveling of leveling stand LS (and hence, plates 120, 130 disposed on leveling stand LS) as described in the Laboratory Examples below.

Sweating hot plate 100, power source PS and water source WS are most suitably surrounded by an enclosure box (not illustrated), preferably made of plexiglass for easy viewing of and for keeping dust off of sweating hot plate 100, power source PS, and water source WS. For the particular sizes of sweating hot plate 100, power source PS, and water source WS, as described herein, the enclosure box has an internal height, width, and depth of 35 cm, 52 cm and 53 cm, respectively. As a result, the enclosure box provides ample room to house leveling stand LS, sweating hot plate 100, power source PS, and water source WS.

Base 124 of inner plate 120 has a centrally placed water inlet port IP (see FIG. 1D) to which a Tygon tube T is attached to connect plate 120 to water source WS. Similarly, guard plate 130 has 4 water inlet ports IP'(see FIG. 1E), one on each of the 4 sides of guard plate 130, to which 4 Tygon tubes T' are attached to connect guard plate 130 to water source WS. Suitably, Tygon tubes T, T' are attached to plates 120, 130 with a silicone sealant.

Figure 2A:
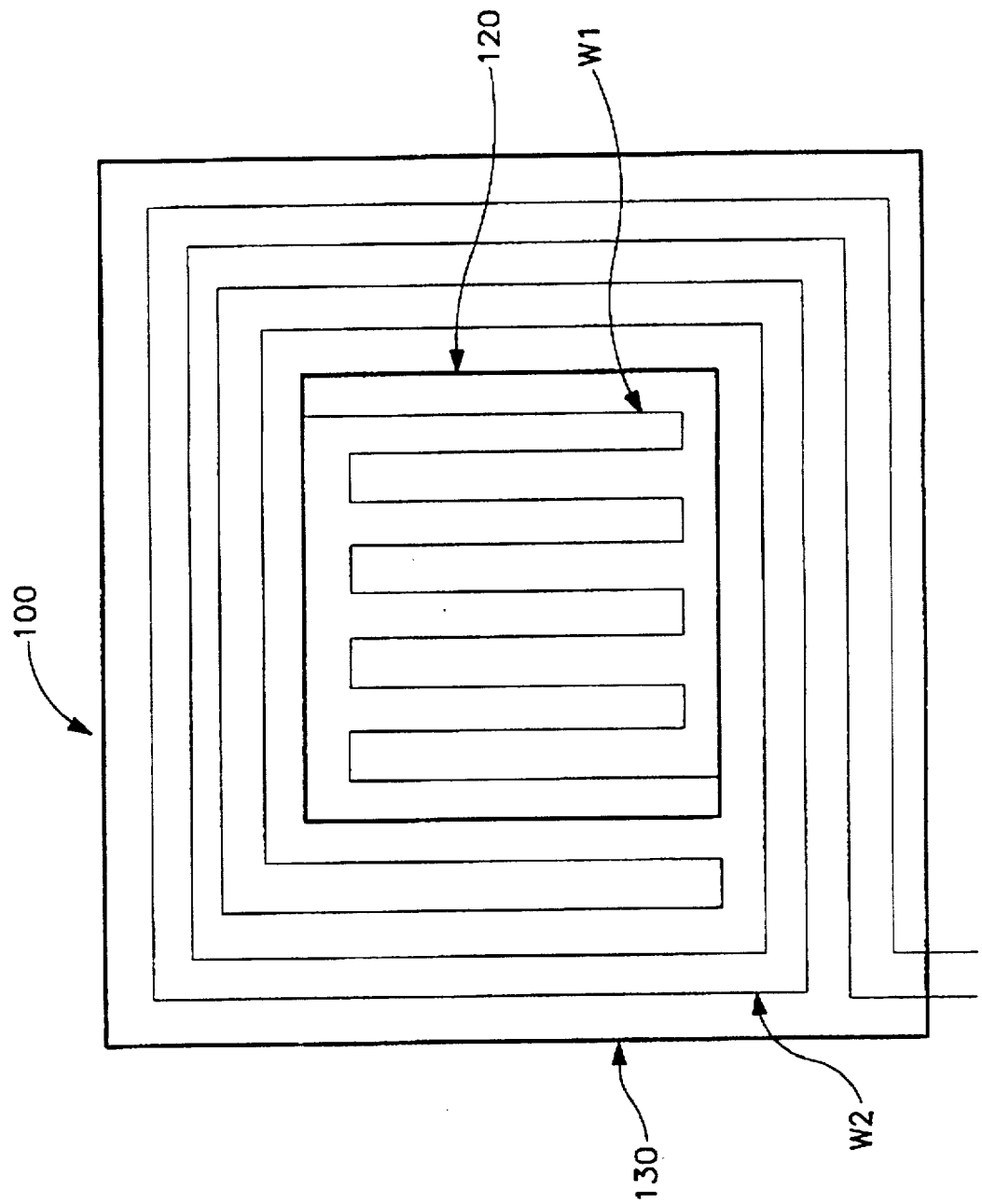
FIG. 2A is a schematic, horizontal cross-sectional view of the wiring beneath the sweating hot plate of FIG. 2.

Heating wires W1, W2 lead to plates 120, 130, respectively. FIG. 2A shows a schematic, view of heating wires W1, W2 beneath plates 120, 130. Preferably, each of heating wires Wi, W2 is 30 gauge wire, having a diameter of 0.01 inch (0.024 cm), and a resistivity of 2.94 Ω/foot (0.0965 Ω/cm).

Wires W1, W2 are arranged (see FIG. 2A) in a rectangular matrix to provide uniform heating of plates 120, 130. Accordingly, a length of wire W1 of 82 cm is employed to connect power source PS and inner plate 120, and a length of 241 cm of wire W2 is employed to connect power source PS and guard plate 130. The length of 82 cm provides a resistance of 7.91 Ω and the length of 241 cm provides a resistance of 23.25 Ω.

As is well known to the person of ordinary skill in the art, Ohm's law provides:

voltage=current×resistance and since both the resistance and the current passing through the 2 lengths of wire W1, W2 are known, the power:

current$^2$×resistance can be easily determined. Also, since the surface area of surfaces 123, 133 (which define the surface of plate 100) is known, the power input:

(current$^2$ ×resistance)/surface area can also be easily determined.

Power source PS includes 2 DC power supplies PS1, PS2, enabling independent power input for each of plates 120, 130, respectively. Suitable power supplies are the ELECTRO INDUSTRIES Model 3002A and the ELENCO PRECISION Model XP-650.

As these particular power supplies have analog displays, exact current settings are difficult, and hence a digital multimeter (not illustrated) is placed in series with each of the heater wires W1, W2, which enables the setting of current accurate to 1/100 ampere. Such digital multimeters are well known to the person of ordinary skill in the art. The range of current typically used for each of inner plate 120 and guard plate 130 ranges between 0.30 and 0.70 A, depending on the metabolic rate (i.e., heat output) of the human being to be simulated, which is described in more detail below in connection with the Laboratory Examples. As is well known to the person of ordinary skill in the art, if power supplies having digital displays are employed, then a digital multimeter is unnecessary.

Also, as is well known to the person of ordinary skill in the art, layers of foam rubber insulation (not illustrated) of about 4 cm in total thickness should be placed about heating wires W1, W2 in order to prevent heat loss. This is achieved by gluing wires W1, W2 to a layer of insulation after pinning wires Wi, W2 into the desired formation, as shown in FIG. 2A. In the preferred embodiment, the layers of insulation are cut large enough to provide an ample amount of lateral insulation. Suitable foam rubber insulation is available from Fisher of Springfield, N. J., and each foam rubber insulation sheet is ½ inch (1.27 cm) thick and has a k-factor of 0.28 (BTU) (inch)/(hour) (foot)$^2$, which translates into a thermal conductivity of 0.04 W/m·°C. While the specific heat of the foam rubber insulation sheet was not given by the manufacturer, the density was listed as 96.1 kg/m$^3$.

The temperature of sweating hot plate 100 is monitored by a single type-K thermocouple T connected to a digital multimeter M having a resolution of ±1° C. Such thermocouples and digital multimeters are well known to the person of ordinary skill in the art. The leads of the thermocouple are arranged to run parallel and very close to surfaces 123, 133 of plates 120, 130 in order to minimize unevenness of fabric F placed onto surfaces 123, 133 of plates 120, 130 during testing of fabric F.

As also shown in FIG. 2, water source WS is suitably a gravity feed system in order to achieve cost effectiveness. As is well known to the person of ordinary skill in the art, a water system with a pump could be employed. However, since that would require a pump and electrical supply for the pump, it would be more costly than a gravity feed system.

As water supply systems are well known to the person of ordinary skill in the art, only the basics of the components of water source WS are illustrated in FIG. 2. Details of water source WS are as follows.

Independent flow control for providing water W to inner plate 120 and guard plate 130 is achieved by employing two fine metering valves V1, V2. For repeatable flow, metering valves V1, V2 were equipped with vernier handles (not illustrated), as is well known to the person of ordinary skill in the art. On these handles are 25 graduations, such that one complete turn is 25 graduations.

Due to the relatively small size of inner plate 120, only a single tube T is employed to connect supply reservoir R of water W vis-a-vis valve VI to the bottom of inner plate 120 at port IP (see FIG. 1D).

The larger, frame-like shape of guard plate 130, however, requires that water W from supply reservoir R is supplied by each of 4 tubes T'. More particularly, by employing small T-fittings (not illustrated), a single tube leaving valve V2 is split into 2 tubes, each of which is split again to provide 4 tubes T' for connecting supply reservoir R vis-a-vis valve V2 to the respective 4 sides of guard plate 130 at each of 4 ports IP' (see FIG. 1E). Equal lengths of each of the 4 tubes T' are employed to ensure equal pressure drops and flow rates through each of the 4 tubes T' for guard plate 130 for a given setting of valve V2.

Tygon tubes T, T' have outer and inner diameters of ⅛ and 1/16 of an inch (0.3175 and 0.1587 cm), respectively.

As is well known to the person of ordinary skill in the art, fine metering valves, such as valves V1, V2, contain delicate stems, and hence, cannot be used as stop valves, as a result of which stop valves must be placed at appropriate positions in tubes T, T'. For instance, a stop valve (not illustrated) is located prior to where each of valves V1, V2 is disposed in each of tubes T, T', respectively. In addition, a stop valve (not illustrated) is placed in each of tubes T, T' a short distance prior to the connection of each of tubes T, T' at ports IP, IP, respectively. The stop valves enable water supply lines T, T' to be disconnected in order to drain water therefrom.

To minimize, and hopefully eliminate, entry of impurities to metering valves V1, V2 where such impurities could eventually cause inconsistent flow, a small filter (not illustrated) is placed between each set of stop and metering valves. Also, the filters help remove tiny air bubbles from the water W which could collect inside metering valves V1, V2 and cause inconsistent flow if allowed to proceed through tubes T, T'. By using distilled water W, the filters only need replacing after extended use.

With a gravity feed water supply system, an essentially constant height differential between the water level at the head of tubes T, T' and at the end of tubes T, T' is necessary to ensure a steady flow. Such is achieved by locating supply reservoir R at the head of tubes T, T' and keeping reservoir R full and overflowing with water W vis-a-vis hose H connecting reservoir R and storage tank ST.

During testing of fabrics F as described in the Laboratory Examples below, a beaker was employed as reservoir R and placed inside of catch basin CB. Excess water W spilling over from reservoir R into catch basin CB was collected with a cup by hand and returned to storage tank ST. A 2 gallon (7.58 liter) plastic container, with an adjustable spigot was used for storage tank ST. Catch basin CB, which held 3 gallons (11.37 liters), was a plastic tub with a lid to help keep dust and other impurities out of water W so that the filter, mentioned above, would need replacing only after extended use. The height differential employed between top surfaces 123, 133 and the bottom of catch basin CB was about 2 feet (about 0.7 meters).

Prior to employing sweating hot plate 100 and associated power supply PS and water source WS to determine thermal comfort characteristics of fabrics F, calibration was accomplished in order to determine flow rates associated with a range of various settings. The calibration procedure is as follows.

Calibration of Sweating Hot Plate Apparatus

Initially, the tubing of the apparatus should be clear of any bubbles and flushed with water while the metering valves are fully opened. Since the flow rates involved are as low as 7.5 milligrams of water per minute, a digital balance with 3-place sensitivity should be employed so that the mass shown on the balance can be noted accurately to the second decimal place.

It is also important to ensure that the height differential between water source WS and hot plate 100 used in calibration is the same as that used in actual testing of fabrics as the water supply is gravity driven. Such can be achieved by placing the balance at a height just below the level of the inner and guard plates. Next, a beaker is placed on the balance and filled with water such that the level in the beaker matches that of the plates. Employing a flat, rigid member and a level, the correct water can be easily determined. The balance must be set up in close proximity to the inner and guard plates during calibration.

The most convenient technique is to note the combined mass of the beaker and water, which matches the level of the inner and guard plates, for reference in each calibration test run. By using this reference point, instead of taring the balance after each test, the correct level can be re-established. While it is assumed that the quantity of water flowing into the beaker during the calibration testing will not significantly alter the height differential, several calibration tests may have some effect. Thus, the reference points should be reestablished frequently.

While the high sensitivity of the 3-place balance is necessary to calibrate the metering valves accurately, the balance is also extremely sensitive to any outside forces acting on it, such as air currents or the tubes supplying the water. The effects of air currents were eliminated by placing a cover or box around the balance. The effects of the water supply tubes were eliminated by allowing the tubes to hang vertically into the beaker. The ends of the tubes were placed below the surface of the water in the beaker, but not touching the bottom or sides of the beaker. Even with these precautions, there was still some minor fluctuation of the digital display. In most cases, the value was estimated to some degree, but generally with an accuracy of ±0.01 gram.

Once the balance was properly shielded, calibration testing began. During the calibration testing, the supply reservoir was kept at a constant level by ensuring that the amount of water flowing into the reservoir was greater than the amount of water flowing out.

Only one of the metering valves was calibrated at a time. First, the metering valve was set to the desired value on the vernier handle. As noted, each turn of the handle is divided into 25 increments, and thus, a setting may be given as a fraction of 25. For instance, a given setting may be 15/25, representing 1 full turn plus 5 increments.

After the metering valve was set, the stop valve near the end of the tube was opened after closing the leading stop valve. Next, the mass shown on the display was recorded, and, at a set time, the leading stop valve was opened. The weight displayed on the balance was recorded to 1/100 gram at regular intervals, such as every 5 minutes. After a specified number of time intervals, the leading stop valve was closed and the final weight recorded.

The mass flow rate was then calculated for each time interval on a non-cumulative basis. This way, it was easy to determine the steadiness of the flow during the calibration test. Although some variation may occur during the testing, for the testing for the present apparatus, variation less than a few hundredths of a gram over a 5-minute time interval was considered acceptable.

Of more concern was variation between calibration test runs at the same metering valve setting. To determine the between-test variation, a number of tests were run for each metering valve setting tested. Generally, the between-test variation was less than 5/100 gram over a 5-minute time interval. After all the tests were completed for the various metering valve settings, an average flow rate for each setting was calculated. Finally, when calibrating the guard plate metering valve, only one of the 4 tubes was used at a time. This approximated the procedure used when operating the apparatus, as described below.

After the calibration, sweating hot plate 100 was employed to simulate human thermoregulatory responses as follows.

LABORATORY EXAMPLES

For all test examples as described below, the following general testing procedures were employed.

The testing procedures were generally independent of the conditions to be simulated, but detailed human subject data was collected in order to ensure accurate simulation. Also, certain steps prior to testing of fabrics were followed in order to make the fabric testing as repeatable as possible.

The first step towards any test is determining the specific conditions to be simulated. The human metabolic and mean sweat rates must be converted into a current setting and a valve setting, respectively, based on calibration data. It is also important to know the ambient conditions during the human subject test, including the air and mean radiant temperatures, relative humidity, and air velocity. If possible, these conditions should be reproduced as accurately as possible.

Reproduction of ambient conditions can be accomplished using an electronically controlled environmental chamber, or, more economically, by selecting human subject tests carried out close to standard laboratory conditions, such as 23° C. air and mean radiant temperatures, 50% relative humidity, and 0.1 meters per second air velocity. However, if this is not possible, then knowing the differences between the conditions will assist in analyzing the sweating hot plate data.

The human subject data should also contain information concerning the mean skin temperature of the subjects, which is usually given for the final time period of the test. The thermal insulation of the clothing, I, which is usually given in clo units, as well as the resistance of the clothing to the passage of water vapor, $R_{ef}$, should be given to allow proper simulation. To test the apparatus in a bare plate state, human data for subjects wearing only shorts, socks, and shoes, or about 0.1 clo, was used.

Although the human subject data employed in the Laboratory Examples below was for selected power and water inputs of: low (116 W/m² and 85 g/h·m²), moderate (206 W/m² and 145 g/h·m²), and high (345 W/m² and 260 g/h·m²), it is to be understood that the invention is not limited thereto. The selected power input may range from 0 to 1,000 W/m² and the selected water input may range from 0 to 450 g/h·m².

The procedures used for testing the sweating hot plate apparatus with the sweating mechanism were much more involved than the procedures that were used for the dry calibration tests. First, the water supply lines were cleared and filled to the edge of the insulation. Next, the sweating mechanism was engaged after the inner and guard plates achieved a selected critical temperature, such as 33° C.

The water supply was set to follow a 20 minutes on and 10 minutes off cycle to ensure a steady flow. Therefore, 150% of the desired average evaporation rate was supplied to the inner and guard plates to account for the time no water was flowing. The 20 minutes on and 10 minutes off cycle was repeated until the inner and guard plates attained an equilibrium surface temperature.

Table A below summarizes all the steps required for conducting tests with and without the sweating mechanism, referred to as wet and dry, respectively.

TABLE A

Sweating Hot Plate Testing Procedures

| DRY | WET | STEPS |
|---|---|---|
| X | X | 1. Determine the required inputs of current and water |
| X | X | 2. Set the DC power supplies to the appropriate current levels |
|   | X | 3. Clear the tubes and valves of any bubbles or impurities |
|   | X | 4. Drain the tube sections directly connected to the plates |
|   | X | 5. Refill tube sections to the edge of the insulation |
|   | X | 6. Set metering valves to a reference setting (5 turns open) |
| X | X | 7. Turn power supplies ON at time zero |
| X | X | 8. Record the plate temperature and ambient conditions, at time zero |
| X | X | 9. Continue recording the plate temperature at regular intervals |
|   | X | 10. At a critical plate temperature, turn the flow to both plates ON |
|   | X | 11. Turn flow OFF when water reaches the plates, a known time |
|   | X | 12. Re-set metering valves to supply 150% of simulated sweat rate |
|   | X | 13. Turn flow to both plates ON, but only one guard tube at a time |
|   | X | 14. After 5 minutes, turn guard plate flow OFF |
|   | X | 15. Re-set guard plate metering valve to reference setting |
|   | X | 16. Turn guard plate flow ON for a different tube |
|   | X | 17. Turn guard plate flow OFF when water reaches the plate |
|   | X | 18. Re-set guard plate metering valve to supply 150% of sweat rate |
|   | X | 19. Turn guard plate flow ON |
|   | X | 20. Repeat Steps 14 and 19 for the last two guard plate tubes |
|   | X | 21. Turn OFF flow to both plates 20 minutes after flow was initiated |
|   | X | 22. Repeat Steps 4 through 6 for both the test and guard plate tubes |
|   | X | 23. Repeat Steps 10 through 21 starting 10 minutes after flow stopped |
|   | X | 24. Repeat 20/10 minute cycle until the plates reach a final temperature |

TABLE B

Human Subject Test Data

| M (W/m²) | $m_{sw}$ (g/h·m²) | $T_{amb}$ (°C.) | RH (%) | $V_{air}$ (m/s) | $T_{skin}$ (°C.) | I (clo) |
|---|---|---|---|---|---|---|
| 116 | 85 | 21 | 28 | 0.32 | 31.3 | 0.1 |
| 206 | 145 | 25 | 47 | 0.30 | 32.6 | 0.1 |
| 345 | 260 | 24 | Unknown | 0.20 | 33.5 | 0.1 | wherein:

M=the heat output of the humans in watts per square meter, and thus the thermal input of power flux supplied to the sweating hot plate during testing of plate (with and without fabrics) as set out further below;

$m_{sw}$=the sweat output of the humans in grams per hour·square meter, and thus the water input of water flow supplied to the sweating hot plate during testing of plate (with and without fabrics) as set out below;

$T_{amb}$=the temperature of the air or room in degrees Centigrade;

RH=the relative humidity of the air or room;

$V_{air}$=velocity of the air in meters per second;

$T_{skin}$=the temperature of the skin of the human in degrees Centigrade; and

I=the thermal insulation of the clothing that the humans were wearing in clo units.

Example 2 (Bare Plate without Fabric)

The tests performed on the sweating hot plate for comparison to human subject data were conducted without any fabric covering or membrane covering on the plate, or in the bare state. Tests were performed, with and without sweating, for each of the 3 activity levels given above. The bare tests were performed for comparison to test data from subjects wearing a minimum of clothing, and thus, data from the bare state is analogous to the human data collected from subjects wearing the 0.1 clo outfit since most of their skin was bare.

With power and water inputs of the plate set to match the heat and sweat outputs, respectively, recorded from the human subjects, the final plate surface temperature was analogous to the final mean skin temperatures of the subjects. Hence, the temperature of the plate, with the sweating engaged, was compared to the mean skin temperature. The tests performed without sweating, i.e., dry calibration tests, serve as a reference to illustrate the cooling effect of the evaporating water.

For the low activity level, with thermal and water inputs of 116 W/m² and 85 g/h·m², respectively, the final surface temperature of the plate was recorded to be 30° C. Compared to a corresponding mean skin temperature of 31.3° C., this showed a difference of only 4.3%.

Figure 3:
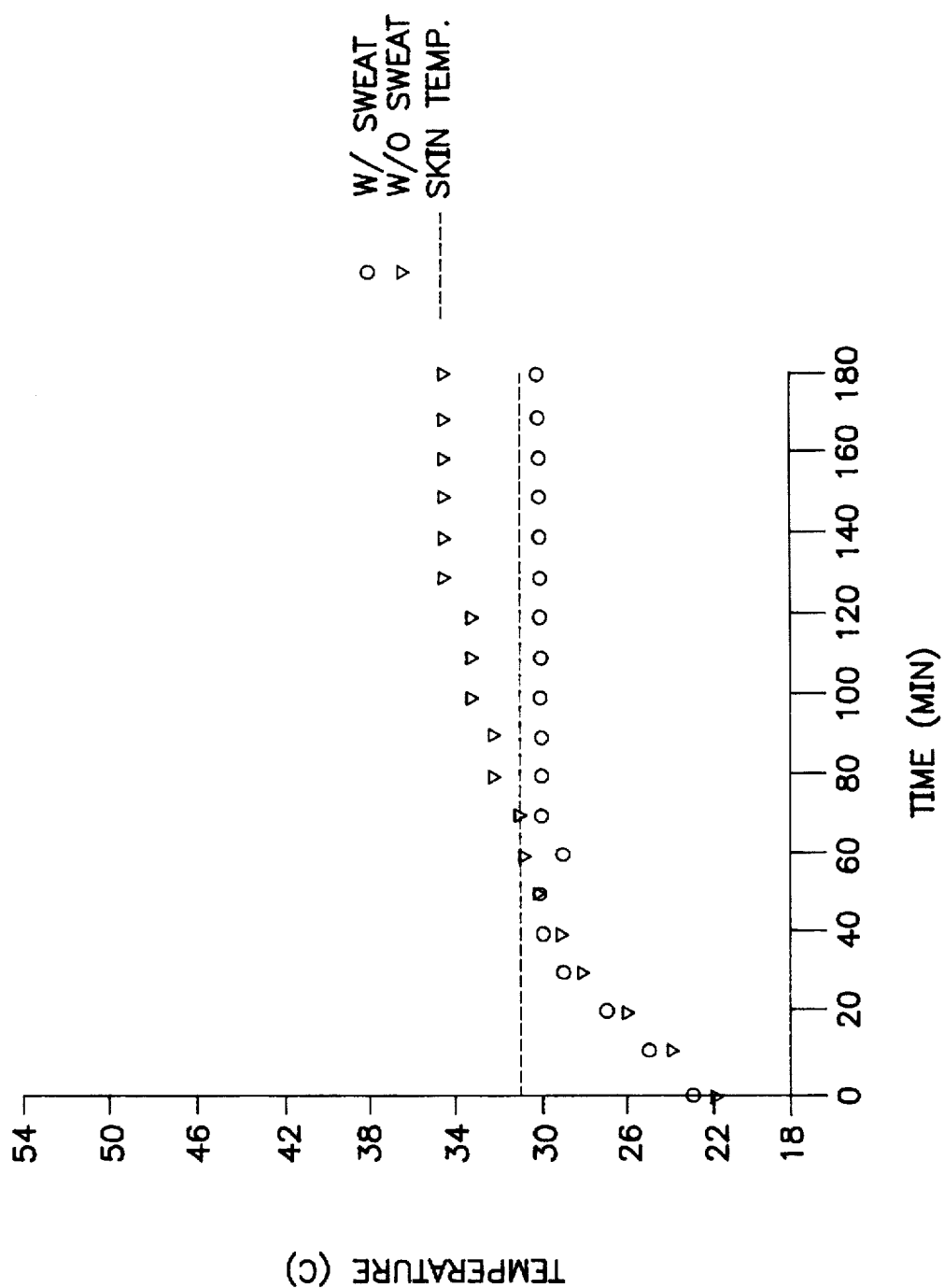
FIG. 3 is a graph showing the change in plate temperature vs. time, with no fabric on the plate and with the power input set at 116 W/m$^2$.

FIG. 3 is a graph of the plate temperature variation with time for both the dry and sweating tests, with no fabric on the plate at a power input of 116 W/m². The dotted line represents the corresponding final mean skin temperature of the human subjects for the low activity level.

At the moderate activity level, with thermal and water inputs of 206 W/m² and 145 g/h·m², respectively, the final surface temperature of the plate leveled off at 31° C. Again, the plate temperature was slightly lower than the mean skin temperature, which was 32.6° C, or a difference of 5.2%. As compared to the low activity level, the cooling effect of the evaporating water was considerably greater at the moderate activity level, reflecting the increased volume of water.

Example 1 (Human Subject Data)

The present apparatus was tested to determine how closely the surface temperature of the plates matched the mean skin temperature of human subjects, under the same inputs and conditions.

Human subject data was obtained for three levels of metabolic activity: low (116 W/m² and 85 g/h·m²), moderate (206 W/m² and 145 g/h·m²), and high (345 W/m² and 260 g/h·m²). In each of these tests, the human subjects exercised on a cycle ergometer wearing shorts, socks and shoes (0.1 clo). Furthermore, the environmental conditions during each test were close to standard laboratory conditions.

The low activity human data was obtained from Olesen et al., "Physiological Comfort Conditions at Sixteen Combinations of Activity, Clothing, Air Velocity, and Ambient Temperature", *ASHRAE Trans.*, reprint no. 2254 (1989); the moderate activity human data was obtained from Holmer et al., "Quantification of Heat Balance During Work in Three Types of Asbestos-protective Clothing", *Int. Arch. Occup. Environ. Health*, Vol. 64, p. 243 (1992); and the high activity human data was obtained from Adams et al., "Effects of Varied Air Velocity on Sweating and Evaporative Rates during Exercise", *J. Appl. Physiol.*, Vol. 73, p. 2668 (1992).

Table B below summarizes the human subject data from these 3 journal articles.

Figure 4:
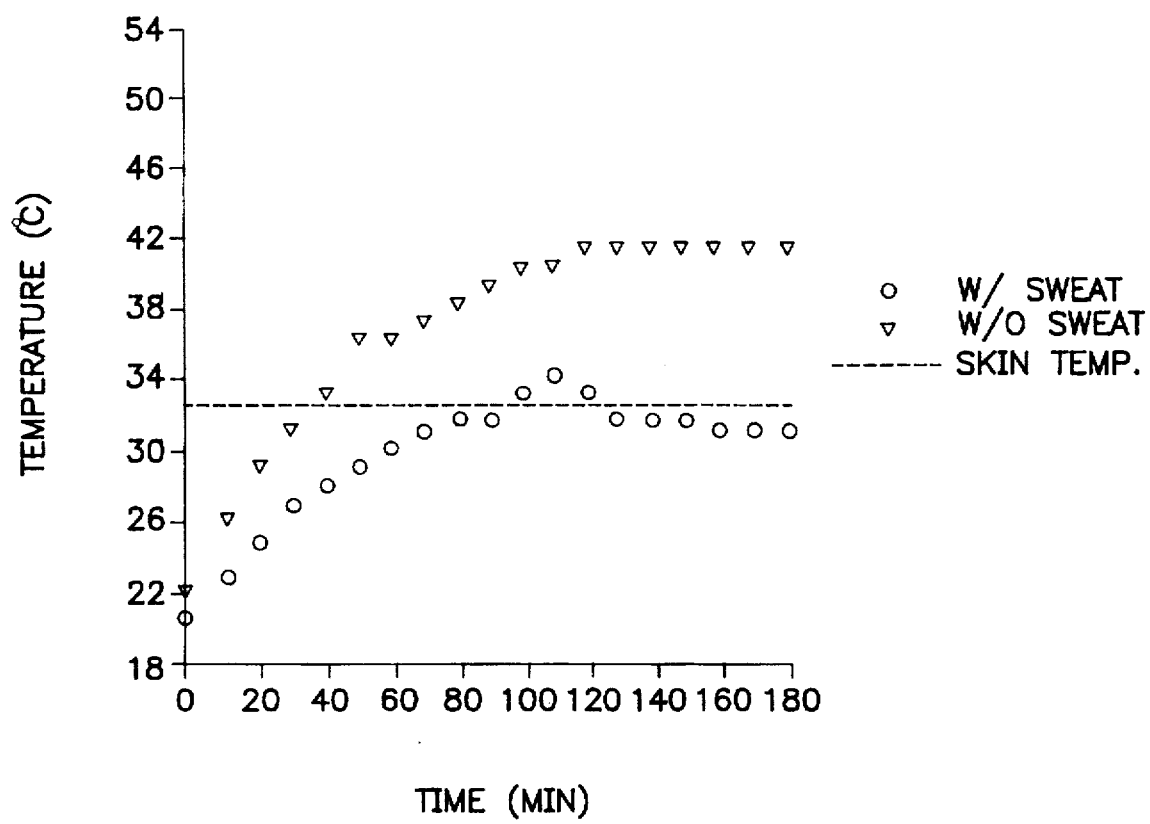
FIG. 4 is a graph showing the change in plate temperature vs. time, with no fabric on the plate and with the power input set at 206 W/M$^2$.

FIG. 4 is a graph of plate temperature variation with time, with no fabric on the plate and 206 W/m² power input. The dotted line represents the corresponding final mean skin temperature of the human subjects for the moderate activity level.

The high activity level, with thermal and water inputs of 345W/m² and 260 g/h•m², respectively, showed very good agreement with the mean skin temperature of the human subjects, 33° C. versus 33.5° C., which was only a 1.5% difference. In addition, the cooling effect was much more pronounced than at either the low or moderate activity levels. This trend suggests that by increasing the water input rate, the surface temperature of the plate can be kept low enough to simulate human skin temperatures even at relatively high power inputs.

Figure 5:
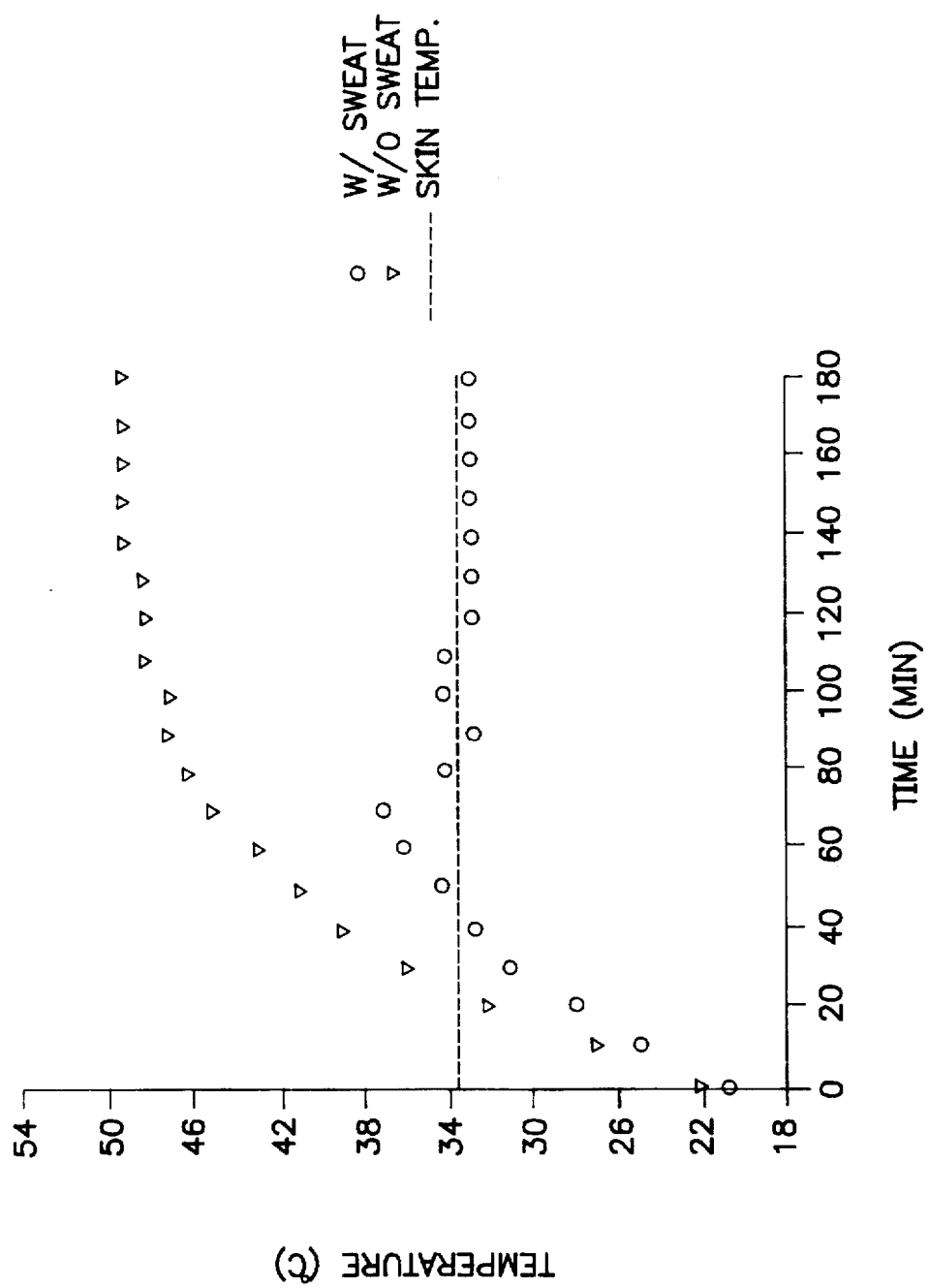
FIG. 5 is a graph showing the change in plate temperature vs. time, with no fabric on the plate and with the power input set at 345 W/m$^2$.

FIG. 5 is a graph of plate temperature variation with time, as well as the corresponding mean skin temperature for the high activity level, with no fabric on the plate and 345 W/m² power input. The dotted line represents the corresponding final mean skin temperature of the human subjects for the high activity level.

Example 3 (Testing of Fabrics on Plate)

Tests were also performed to determine if the sweating hot plate apparatus would respond appropriately to fabrics with a range of thermal and moisture vapor resistance values. These tests were performed on a qualitative basis, where the order of the test fabrics, under given input conditions, was the only issue of interest. Fabrics, with the necessary range of properties, were tested with inputs to the plate corresponding to the moderate activity level.

Table C below lists the thermal and moisture resistance values of the 3 fabric samples, as well as a brief description of their compositions.

TABLE C

Test Fabric Compositions and Properties

| Fabric | Composition | I (clo) | $R_{ef}$ (m²kPa/W) |
|---|---|---|---|
| 1 | 3.2 oz/yd² Neoprene ® and Nomex ® | 0.08 | 0.142 |
| 2 | 3.0 oz/yd² Goretex ® and Kevlar ®/PBI ® | 0.18 | 0.006 |
| 3 | 7.0 oz/yd² Nomex ® quilt | 0.40 | 0.005 | wherein:

I=the thermal insulation of the fabric in clo units;

$R_{ef}$=the resistance of the fabric to the passage of water in square meters•kiloPascals/Watt.

As with testing of the bare plate, each of the 3 fabric samples was tested with and without the sweating mechanism to determine if the sweating hot plate apparatus responded appropriately to fabrics with a range of properties. Each of the 3 fabric samples was cut to the same dimensions as the outside of the guard plate, namely 20 cm×20 cm, to ensure no lateral heat flow, and were tested under the moderate activity level inputs (with thermal and water inputs of 206 W/m² and 145 g/h•m², respectively) and under the high activity level inputs (with thermal and water inputs of 345 W/m² and 260 g/h•m², respectively) used in the bare plate tests. These inputs were selected so that the bare test data could serve as a reference.

Figure 6:
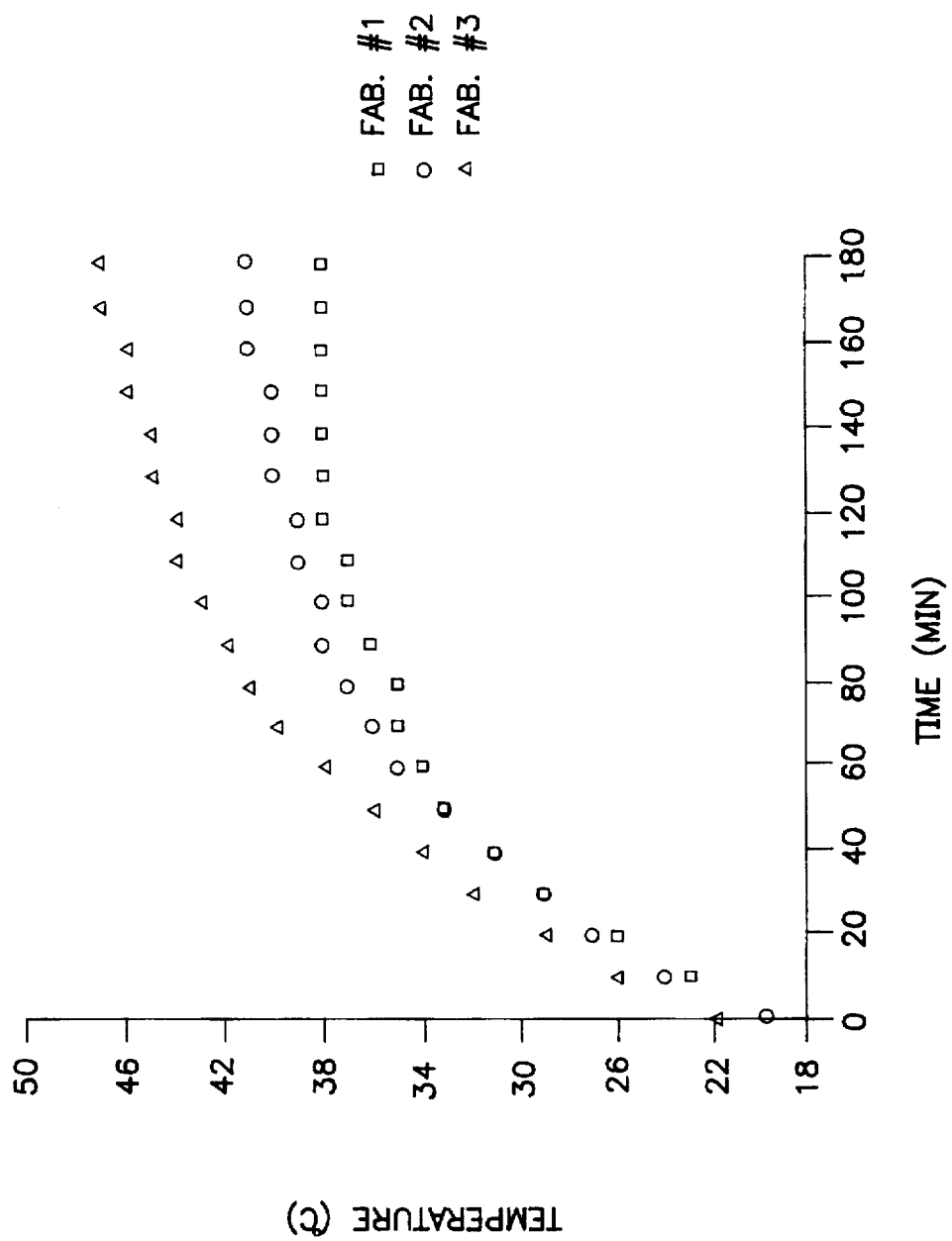
FIG. 6 is a graph showing the change in plate temperature vs. time, with each of the 3 tested fabrics on the plate, with no sweating and with a power input set at 206 W/M$^2$.

For the moderate level inputs, Fabric 3 showed a profile with the highest temperature when the test was performed without sweating. The profile of Fabric 2 demonstrated the second highest temperature, followed by Fabric 1. This order is appropriate for the thermal resistance values given for the fabrics, and the differences in the final plate temperatures among the 3 fabrics corresponded to the differences in their thermal resistances as can be seen in FIG. 6, which is a graph of change in plate temperature with time, for each of the fabrics, with no sweating of the plate at a power input of 206 W/m².

Figure 7:
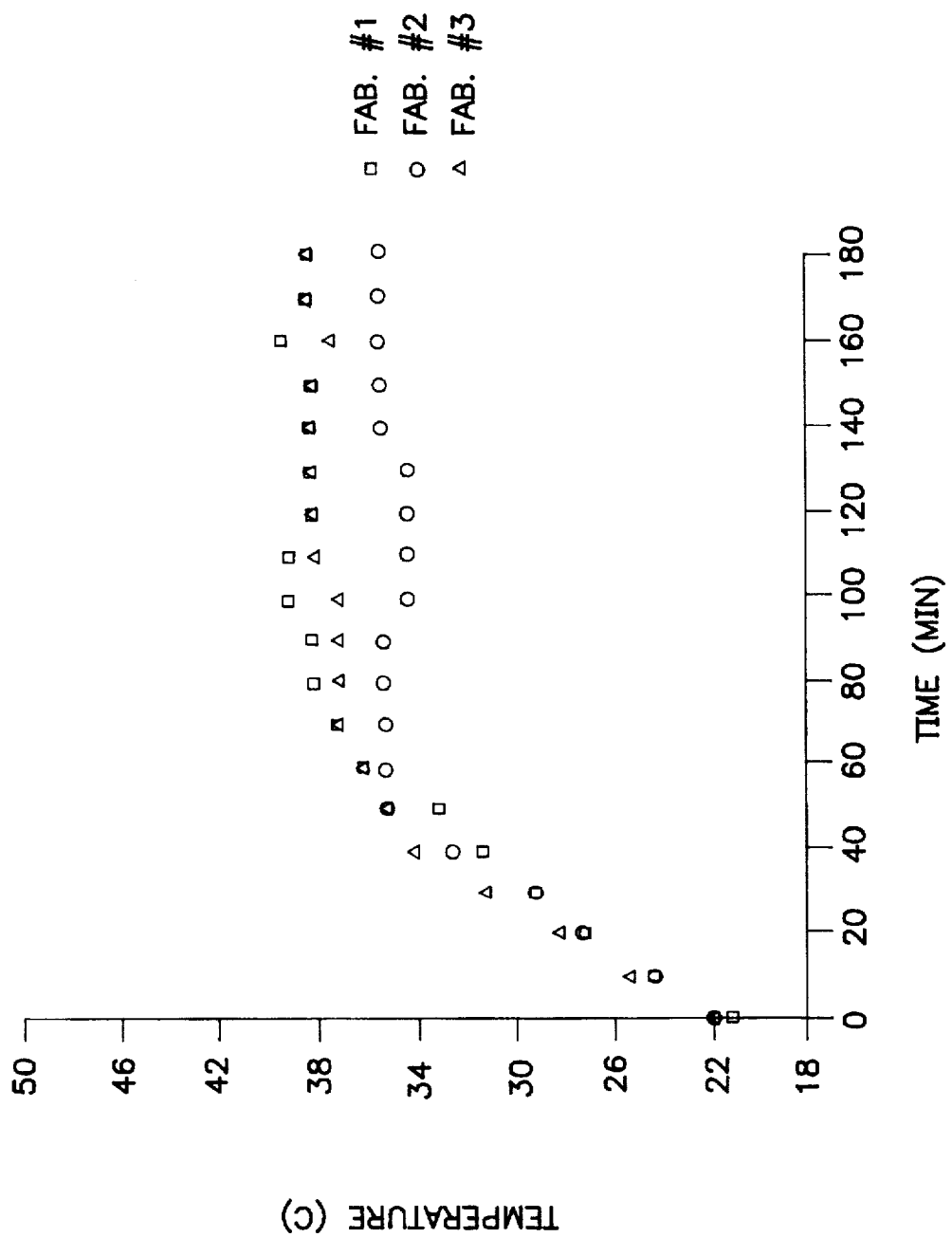
FIG. 7 is a graph showing the change in plate temperature vs. time, with each of the 3 tested fabrics on the plate, with sweating and with a power input set at 206 W/m$^2$.

When the sweating mechanism was engaged, however, the order changed. The final temperatures of Fabric 1 and Fabric 3 were virtually identical. Although Fabric 1 had only ¼ the thermal resistance of Fabric 3, the impermeable nature of Fabric 1 (the resistance of Fabric 1 to the passage of water is a relatively high 0.142 m²kPa/W, as compared to 0.006 m²kPa/W and 0.005 m²kPa/W for Fabrics 2 and 3, respectively) meant water could easily evaporate from the plate surface. Fabric 2, with a fairly low thermal resistance and good vapor permeability, displayed the lowest temperature profile. FIG. 7, which is a graph of change in plate temperature with time, for each of the fabrics, with sweating of the plate at a power input of 206 W/m², illustrates the temperature profiles of each fabric when the sweating mechanism was used.

The tests performed at power and water inputs corresponding to the high activity level were in agreement with those performed at the moderate level. Again, the temperature profiles of each of the 3 fabrics, when sweating was not used, corresponded to the thermal resistance values of each of the 3 fabrics. Of course, the final plate temperatures were significantly higher for each fabric compared to the moderate activity level, due to the increased power input.

Figure 8:
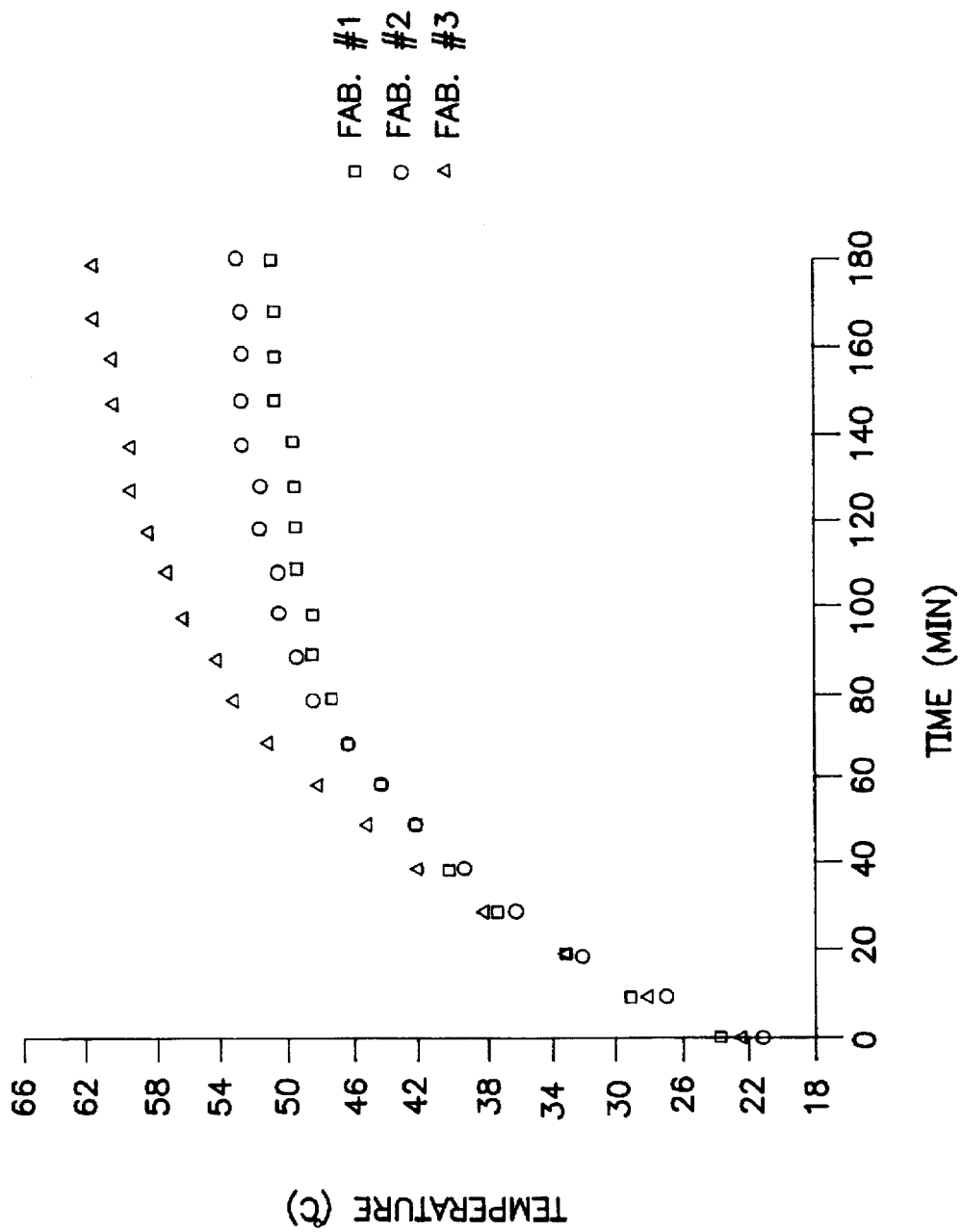
FIG. 8 is a graph showing the change in plate temperature vs. time, with each of the 3 tested fabrics on the plate, with no sweating and with a power input set at 345 W/m$^2$.

FIG. 8, which is a graph of change in plate temperature with time, for each of the fabrics, with no sweating of the plate at a power input of 345 W/m², shows the temperature profiles of all 3 fabrics, without sweating. Once again, Fabric 3 had a profile with the highest final temperature; fabric 2 had the next highest temperature profile; and Fabric 3 had the lowest temperature profile.

Figure 9:
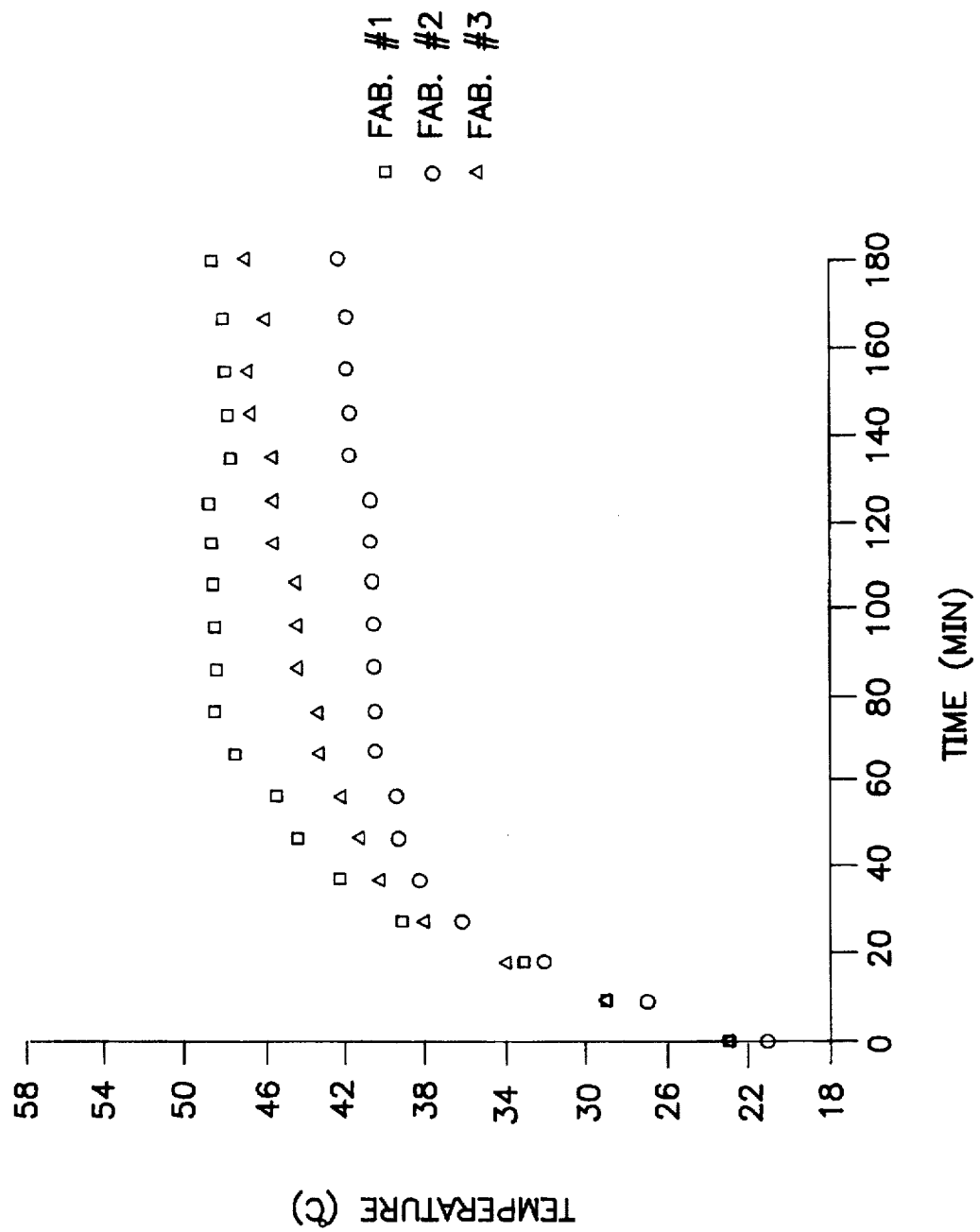
FIG. 9 is a graph showing the change in plate temperature with time, with each of the 3 tested fabrics on the plate, with sweating and with a power input set at 345 W/m$^2$.

When the sweating function was used, the lack of water vapor permeability of Fabric 1 became even more evident. Fabric 3, with four times the thermal resistance of Fabric 1, actually showed a lower final temperature. This was a result of the impermeability of Fabric 1, and after sweating tests with Fabric 1 were concluded, the down-side of the fabric was found to be saturated with liquid water. Again, as expected, Fabric 2 showed the lowest final temperature, due to its relatively low thermal resistance and good water vapor permeability. The temperature profiles of each of the 3 fabrics, with sweating, are shown in FIG. 9, which is a graph of the change in plate temperature with time, for each of the fabrics, with sweating of the plate at a power input of 345 W/m².

The relationship between thermal resistance and the final plate temperature was also plotted directly, both with and without sweating of the plate.

Figure 10:
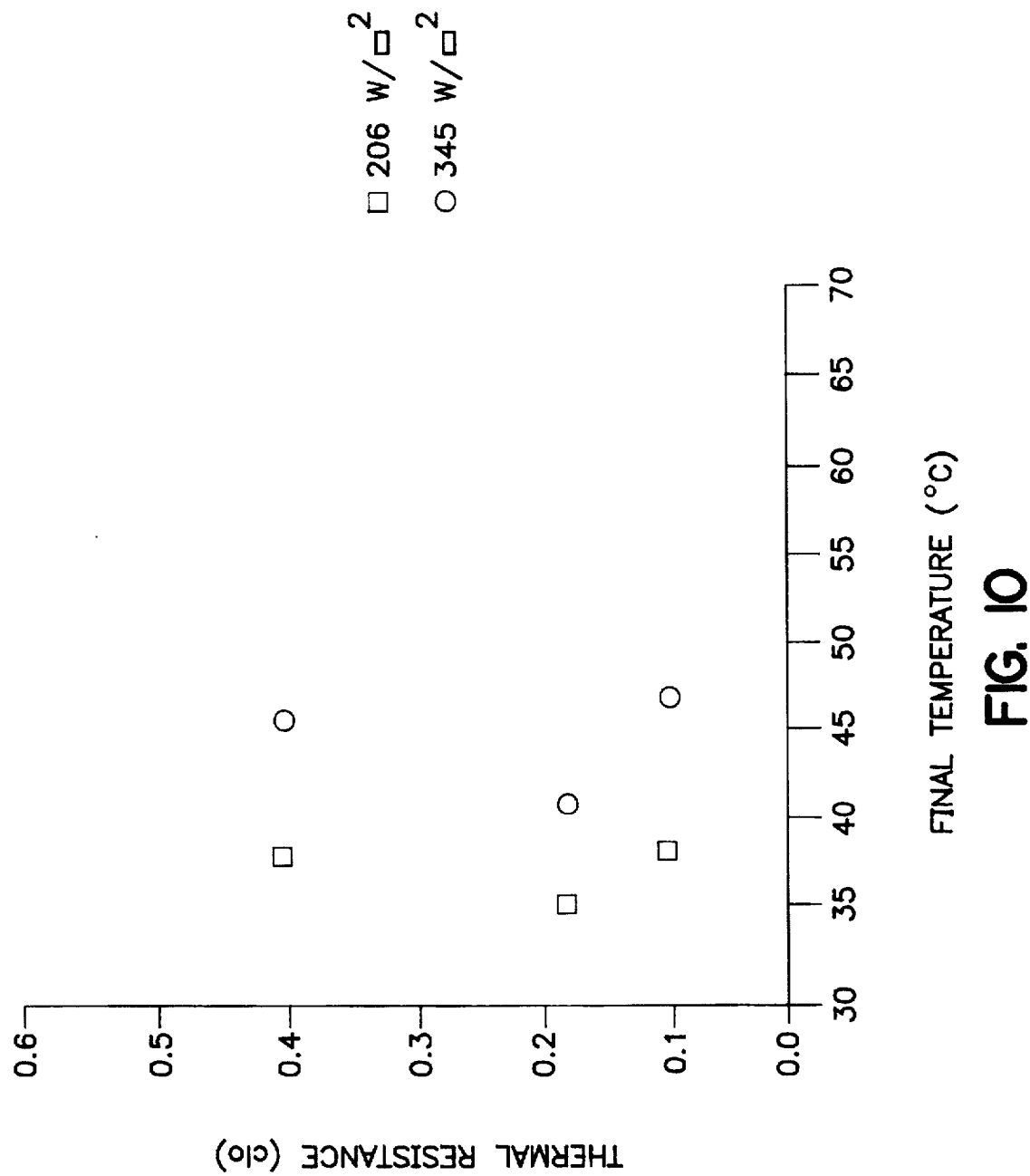
FIG. 10 is a graph showing the thermal resistance of each of the 3 tested fabrics at the final plate temperature, with sweating.
Figure 11:
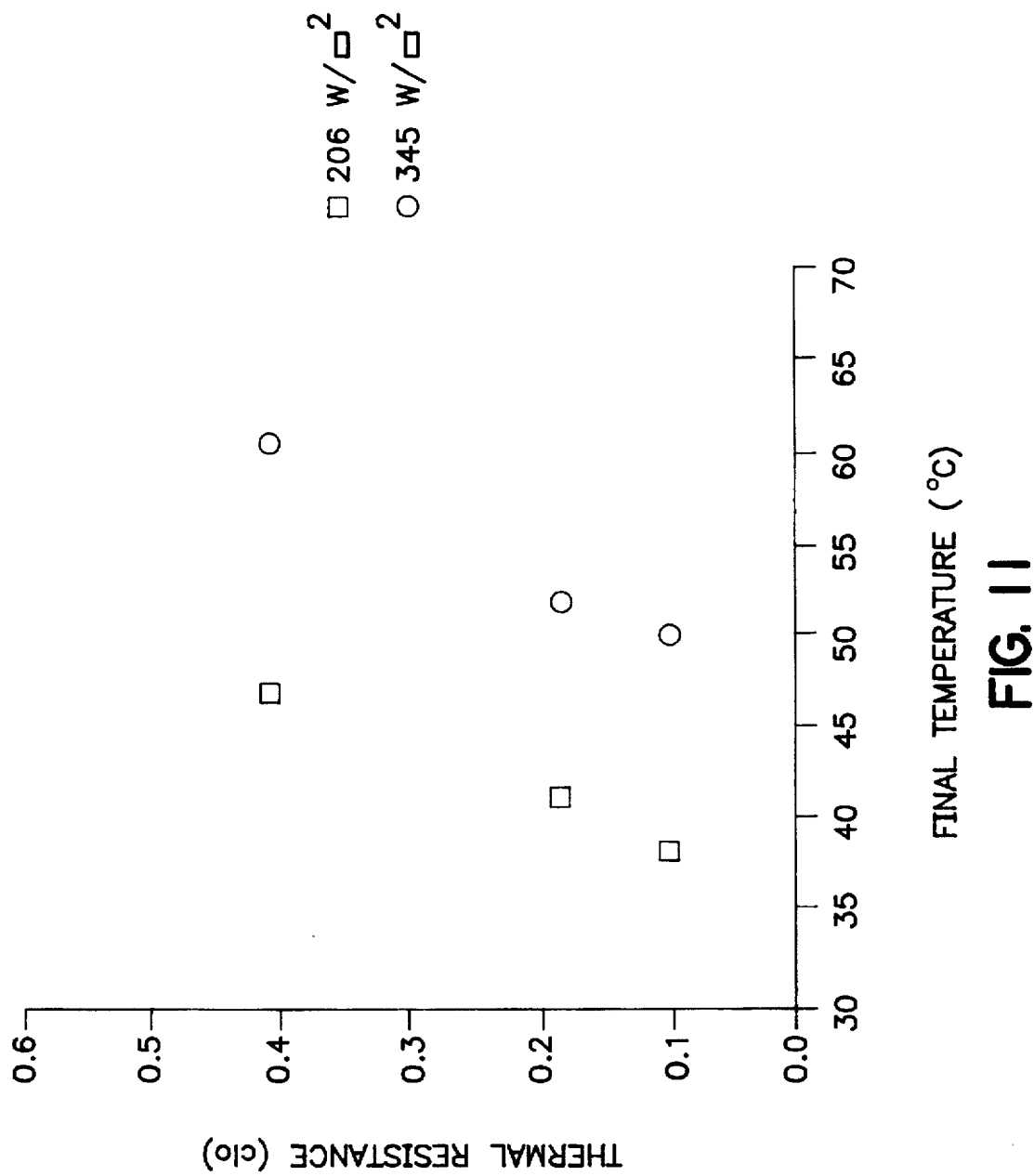
FIG. 11 is a graph showing the thermal resistance of each of the 3 tested fabrics at the final plate temperature, without sweating.

When the sweating mechanism was used, as seen in FIG. 10, which is a graph of thermal resistance with final plate temperature, with sweating, the final temperature of the plate was skewed to the right for the lowest thermal resistance value. This value corresponded to Fabric 1, whose impermeable nature caused the final temperature of plate to be higher. In contrast, when sweating was not used, as seen in FIG. 11, which is a graph of thermal resistance with final plate temperature without sweating, the plot of thermal resistance with final temperature formed a relatively straight line.

Based on these tests, it is clear that the final surface temperature of the plate is a close approximation of the mean skin temperature of the human subjects under the inputs and conditions similar to that of 3 different activity levels, where the human subjects were wearing clothing with 0.1 clo thermal resistance.

The sweating function of the apparatus was shown to be highly effective for cooling the surface of the plate, as can be seen from the differences between the final plate temperatures with and without sweating. Furthermore, by increasing the amount of water input, a surface temperature similar to that of human skin can be achieved even at relatively high power input levels.

Moreover, both at the moderate and high activity level settings, the sweating hot plate responded appropriately to the type of fabric on top of it. For fabrics with increasing thermal resistance values, there was a corresponding increase in the final temperature of the plate. Furthermore, a lack of water vapor permeability was shown to cause the final temperature of the plate to approach a limit corresponding to the temperature profile without sweating.

More particularly, with regard to testing conducted with a fabric on the top surface of the sweating hot plate, the apparatus was shown to respond in an appropriate manner. The final temperature of the plate increased in a manner corresponding to the thermal resistance of the fabric, under dry conditions. When the sweating function was used, the effect of water vapor permeability was demonstrated. This was accomplished by showing that a fabric (Fabric 3) with a low thermal resistance, but also a very low water vapor permeability, achieved a final temperature equal to or larger than the final temperature of a fabric (Fabric 1) with four times the thermal resistance, but with a good permeability. Therefore, it can be concluded that the sweating hot plate apparatus can be used with a fabric covering.

As can be seen from the above testing of fabrics, sweating hot plate apparatus 100 predicted the thermal comfort of a fabric directly. The plate obtained a surface temperature that closely approximated the mean skin temperature of the human subjects, given the same inputs and conditions. Accordingly, once the plate approximated the skin temperature, the surface temperature of the plate could be compared to a selected critical temperature. If the plate was below the critical temperature, the fabric was regarded as comfortable for the given activity level and set of environmental conditions. If the plate temperature was above the critical value, the fabric was regarded as uncomfortable for the given activity level and set of environmental conditions.

Therefore, applicants have discovered a novel sweating hot plate apparatus that provides a novel means of simulating the thermal responses of human skin, over a range of activity levels. Similar tests could be performed to correspond to other activity levels, including sedentary and very heavy activity, and to correspond to humans wearing clothing with a different clo unit value, and should give appropriate results.

Thus, the inventive apparatus simulates human metabolic heat generation by receiving a constant power input. The invention simulates average human sweat rates by receiving an equivalent input of water. Prior art sweating hot plates do not supply constant inputs of power and water, but vary them to maintain constant surface temperature. Prior art sweating hot plates determine fabric properties, but, in addition to fabric properties, the inventive apparatus and method provides a tool to directly predict thermal comfort.

It will be understood that various details of the invention may be changed without departing from the scope of the invention. Furthermore, the foregoing description is for the purpose of illustration only, and not for the purpose of limitation—the invention being defined by the claims.

What is claimed is:

1. A sweating hot plate apparatus having a top surface adapted to change temperature for simulation of skin surface thermoregulatory responses of a human, the apparatus comprising:
    (A) an inner plate including (i) a fluid permeable top layer having a top surface, (ii) a base layer having one or more channels disposed therein, and (iii) a circumference and a bottom;
    (B) a guard plate surrounding the circumference and the bottom of the inner plate and including (i) a fluid permeable top layer having a top surface, and (ii) a base layer having one or more channels disposed therein;
    (C) the top surface of the sweating hot plate being defined by the inner plate top surface and the guard plate top surface;
    (D) a fluid input source connected to the inner plate base layer and the guard plate base layer to provide a selected fluid flow to the one or more channels of the inner plate and the one or more channels of the guard plate;
    (E) a thermal input source electrically connected to the sweating hot plate to provide a selected constant power flux to the inner plate and the guard plate; and
    (F) a temperature sensor operatively connected to the surface of the sweating hot plate to determine the temperature thereof.

2. The plate of claim 1, wherein a paper element is sandwiched between the top layer and the base layer of each of the inner plate and the guard plate.

3. The plate of claim 1, wherein the inner plate fluid permeable top layer is porous metal.

4. The plate of claim 3, wherein the inner plate fluid permeable top layer is porous stainless steel.

5. The plate of claim 1, wherein the guard plate fluid permeable top layer is porous metal.

6. The plate of claim 5, wherein the guard plate fluid permeable top layer is porous stainless steel.

7. The plate of claim 1, wherein the inner plate base layer is metal.

8. The plate of claim 7, wherein the inner plate base layer is aluminum.

9. The plate of claim 1, wherein the guard plate base layer is metal.

10. The plate of claim 9, wherein the guard plate base layer is aluminum.

11. The plate of claim 1, wherein the inner plate comprises a plurality of sides around the circumference thereof and the guard plate comprises a plurality of sides adjacent to and spaced-apart from the sides of the inner plate that surround the circumference of the inner plate, and wherein the sides of the inner plate and the sides of the guard plate are separated by an air gap.

12. The plate of claim 1, wherein the fluid provided to the sweating hot plate is water.

13. The plate of claim 1, wherein the fluid input source is selected from the group consisting of a pump system and a gravity feed system.

14. The plate of claim 1, wherein the fluid input source provides fluid to the channels at a flow rate selected from the group consisting of 85 g/h•m$^2$, 145 g/h•m$^2$, and 260 g/h•m$^2$.

15. The plate of claim 1, wherein the thermal input source is selected from one or more DC power supplies connected to the sweating hot plate by one or more wires disposed beneath the inner plate and the guard plate.

16. The plate of claim 1, wherein the thermal input source provides a power flux selected from the group consisting of 116 W/m$^2$, 206 W/m$^2$, and 345 W/m$^2$.

17. A method for predicting the thermal comfort of a fabric comprising:
- (A) providing a sweating hot plate apparatus having a top surface adapted to change temperature for simulation of skin surface thermoregulatory responses of a human, the apparatus including:
  - (i) an inner plate including (a) a fluid permeable top layer having a top surface, (b) a base layer having one or more channels disposed therein, and (c) a circumference and a bottom;
  - (ii) a guard plate surrounding the circumference and the bottom of the inner plate and including (a) a fluid permeable top layer having a top surface, and (b) a base layer having one or more channels disposed therein;
  - (iii) the top surface of the sweating hot plate being defined by the inner plate top surface and the guard plate top surface;
  - (iv) a fluid input source connected to the inner plate base layer and the guard plate base layer to provide a selected fluid flow to the one or more channels of the inner plate and the one or more channels of the guard plate;
  - (v) a thermal input source electrically connected to the sweating hot plate to provide a selected constant power flux to the inner plate and the guard plate; and
  - (vi) a temperature sensor operatively connected to the surface of the sweating hot plate to determine the temperature thereof;
- (B) providing a fluid flow through the fluid input source and providing a power flux through the thermal input source at preselected and constant levels, respectively, corresponding to a predetermined human sweating output level and thermal output level, respectively;
- (C) placing a fabric on the top surface of the sweating hot plate;
- (D) observing the changing temperature of the top surface of the sweating hot plate as the temperature changes to simulate the human skin surface thermoregulatory responses; and
- (E) analyzing the changing temperature of the top surface of the sweating hot plate and determining therefrom the comfort level of the fabric.

18. The method of claim 17, wherein the predetermined human sweating output level and thermal output level are determined at 0.1 clo.

19. The method of claim 17, wherein a paper element is sandwiched between the top layer and the base layer of each of the inner plate and the guard plate.

20. A method for predicting the thermal comfort of fabric comprising:
- (A) providing a sweating hot plate apparatus having a top surface adapted to change temperature for simulation of skin surface thermoregulatory responses of a human, the apparatus including:
  - (i) an inner plate including (a) a fluid permeable top layer having a top surface, (b) a base layer having one or more channels disposed therein, and (c) a circumference and a bottom;
  - (ii) a guard plate surrounding the circumference and the bottom of the inner plate and including (a) a fluid permeable top layer having a top surface, and (b) a base layer having one or more channels disposed therein;
  - (iii) the top surface of the sweating hot plate being defined by the inner plate top surface and the guard plate top surface;
  - (iv) a thermal input source electrically connected to the sweating hot plate to provide constant power flux to the inner plate; and
  - (v) a temperature sensor operatively connected to the surface of the sweating hot plate to determine the temperature thereof;
- (B) providing a power flux through the thermal input source at a preselected and constant level corresponding to a predetermined human thermal output level, respectively;
- (C) placing a fabric on the top surface of the sweating hot plate;
- (D) observing the changing temperature of the top surface of the sweating hot plate as the temperature changes to simulate the human skin surface thermoregulatory responses; and
- (E) analyzing the changing temperature of the top surface of the sweating hot plate and determining therefrom the comfort level of the fabric.

* * * * *